US008520920B2

(12) United States Patent
Guehring et al.

(10) Patent No.: US 8,520,920 B2
(45) Date of Patent: Aug. 27, 2013

(54) SYSTEM FOR DYNAMICALLY IMPROVING MEDICAL IMAGE ACQUISITION QUALITY

(75) Inventors: Jens Guehring, Monmouth Junction, NJ (US); Peter Weale, Chicago, IL (US); Sven Zuehlsdorff, Chicago, IL (US)

(73) Assignees: Siemens Corporation, Iselin, NJ (US); Siemens Medical Solutions USA, Inc., Malvern, PA (US)

( * ) Notice: Subject to any disclaimer, the term of this patent is extended or adjusted under 35 U.S.C. 154(b) by 444 days.

(21) Appl. No.: 12/897,878

(22) Filed: Oct. 5, 2010

(65) Prior Publication Data

US 2011/0110572 A1 May 12, 2011

Related U.S. Application Data

(60) Provisional application No. 61/260,035, filed on Nov. 11, 2009.

(51) Int. Cl.
*G06K 9/00* (2006.01)
*A61B 5/00* (2006.01)

(52) U.S. Cl.
USPC .......... 382/128; 600/300

(58) Field of Classification Search
USPC .......... 382/128–132, 190, 100; 705/2–3; 600/300–301
See application file for complete search history.

(56) References Cited

U.S. PATENT DOCUMENTS

| | | | | |
|---|---|---|---|---|
| 5,986,662 | A * | 11/1999 | Argiro et al. | 345/424 |
| 6,768,811 | B2 * | 7/2004 | Dinstein et al. | 382/128 |
| 6,813,374 | B1 | 11/2004 | Karimi et al. | |
| 6,970,606 | B2 | 11/2005 | Lee et al. | |
| 6,987,892 | B2 * | 1/2006 | Edgar | 382/254 |
| 7,426,567 | B2 * | 9/2008 | Wortmann et al. | 709/231 |
| 7,602,987 | B2 * | 10/2009 | Kuramoto | 382/254 |
| 7,864,993 | B2 * | 1/2011 | Maack et al. | 382/128 |
| 8,040,406 | B2 * | 10/2011 | Enomoto | 348/246 |
| 2003/0039403 | A1 * | 2/2003 | Robins | 382/275 |

OTHER PUBLICATIONS

Jeffrey P. Johnson, et al., "Human Visual System Modeling for Selecting the Optimal Display for Digital Radiography", International Congress Series 1268 (2004) 335-340.

* cited by examiner

*Primary Examiner* — Shefali Goradia
(74) *Attorney, Agent, or Firm* — Joshua B. Ryan

(57) ABSTRACT

A system dynamically improves quality of medical images using at least one processing device including an image analyzer, a correction processor and a message generator. The image analyzer automatically parses and analyzes data representing an image of a particular anatomical feature of a patient acquired by a medical image acquisition device to identify defects in the image by examining the data representing the image for predetermined patterns associated with image defects. The correction processor uses a predetermined information map associating image defects with corresponding corrective image acquisition parameters to determine corrected image acquisition parameters for use in re-acquiring an image using the image acquisition device in response to an identified defect. The message generator generates a message for presentation to a user indicating an identified defect and suggesting use of the corrected image acquisition parameters for re-acquiring an image.

22 Claims, 11 Drawing Sheets

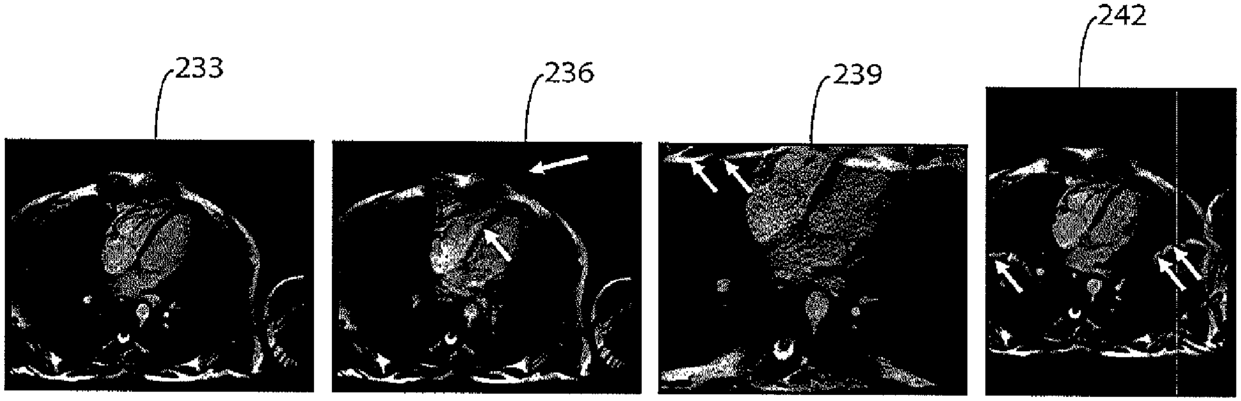

| | Reference Image | Image | Image | Image |
|---|---|---|---|---|
| 203 Artifacts | n/a | Blurry Septum, Myocardium, chest wall | Cropped heart, Aliasing | Aliasing of surrounding tissue |
| 206 Reason | n/a | No, poor breath hold | Field of View (FOV) too small | Incorrect Phase Encoding direction |
| 209 Solution | n/a | Data acquisition during breath hold | Increase FOV, correct slice position | Correct Phase Endcoing direction (e.g. Anterior-posterior) |

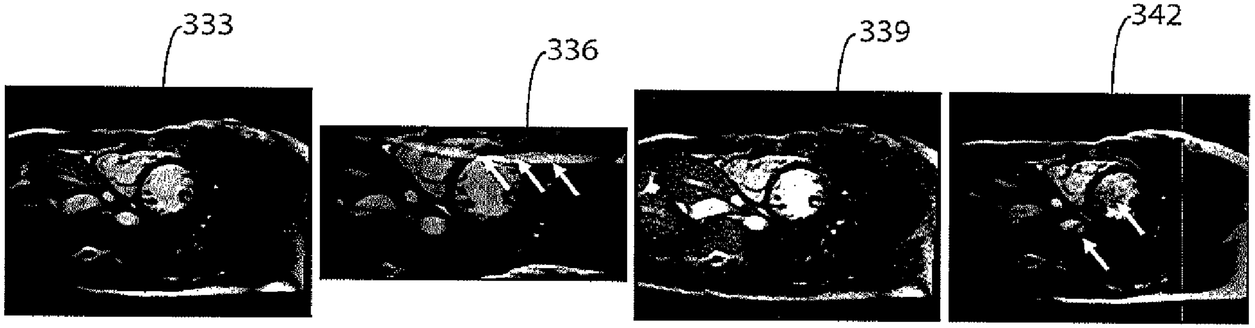

| | Reference Image | Image | Image | Image |
|---|---|---|---|---|
| Artifacts | n/a | Aliasing of surrounding tissue | Low signal to noise ratio | Inhomogeneous blood pool, pulsation artifacts, banding artifacts |
| Reason | n/a | Field of View (FOV) in phase encoding (PE) direction too small | Use of inappropriate coils | Incorrect carrier frequency |
| Solution | n/a | Increase FOV in PE direction | Use appropriate receiver coils/correct coils location | Correct carrier frequency, use frequency scout |

FIGURE 4A

| | Tag | Description | | Content |
|---|---|---|---|---|
| | 0008,0012 | Instance Creation Date | DA | 1 20080221 |
| | 0008,0018 | SOP Instance UID | UI | 1 1.3.12.2.1107.5.99.2.1721.30000008041615245393700001116 |
| | 0008,0020 | Study Date | DA | 1 20080221 |
| | 0008,0021 | Series Date | DA | 1 20080416 |
| | 0008,0022 | Acquisition Date | DA | 1 20080221 |
| | 0008,0023 | Content Date | DA | 1 20080416 |
| | 0008,0030 | Study Time | TM | 1 102921.109000 |
| | 0008,0031 | Series Time | TM | 1 142803.718000 |
| | 0008,0032 | Acquisition Time | TM | 1 115041.715000 |
| | 0008,0033 | Content Time | TM | 1 142804.078000 |
| | 0008,0050 | Accession Number | SH | 1 |
| 403 | **0008,0060** | **Modality** | **CS** | **1 MR** |
| 406 | **0008,0070** | **Manufacturer** | **LO** | **1 SIEMENS** |
| | 0008,0090 | Referring Physician's Name | PN | 1 |
| 409 | **0008,1090** | **Manufacturer's Model Name** | **LO** | **1 Avanto** |
| | 0008,2111 | Derivation Description | ST | 1 Force Anonymity |
| | 0010,0010 | Patient's Name | PN | 1 Test |
| | 0010,0020 | Patient ID | LO | 1 Anonymous |
| | 0010,0030 | Patient's Birth Date | DA | 1 |
| | 0010,0040 | Patient's Sex | CS | 1 O |
| | 0010,1080 | Military Rank | LO | 1 7373294 |
| | 0010,1081 | Branch of Service | LO | 1 O |
| 410 | **0018,0010** | **Contrast/Bolus Agent** | **LO** | **1 with contrast** |
| 410 | **0018,0020** | **Scanning Sequence** | **CS** | **1 RM** |
| 410 | **0018,0021** | **Sequence Variant** | **CS** | **2 SK\SP** |
| 410 | **0018,0022** | **Scan Options** | **CS** | **1 CT** |
| 410 | **0018,0023** | **MR Acquisition Type** | **CS** | **1 2D** |
| 410 | **0018,0024** | **Sequence Name** | **SH** | **1 *fl2d1_v150in** |
| 410 | **0018,0025** | **Angio Flag** | **CS** | **1 N** |
| 410 | **0018,0050** | **Slice Thickness** | **DS** | **1 6** |
| 410 | **0018,0080** | **Repetition Time** | **DS** | **1 36.6** |
| 410 | **0018,0081** | **Echo Time** | **DS** | **1 2.98** |
| 410 | **0018,0083** | **Number of Averages** | **DS** | **1 2** |
| 410 | **0018,0084** | **Imaging Frequency** | **DS** | **1 63.676153** |
| 410 | **0018,0085** | **Imaged Nucleus** | **SH** | **1 1H** |
| 410 | **0018,0086** | **Echo Numbers** | **IS** | **1 1** |
| 410 | **0018,0087** | **Magnetic Field Strength** | **DS** | **1 1.5** |

FIGURE 4B

| | Tag | Description | | | Content |
|---|---|---|---|---|---|
| | 0018,0089 | Number of Phase Encoding Steps | IS | 1 | 138 |
| | 0018,0091 | Echo Train Length | IS | 1 | 1 |
| | 0018,0093 | Percent Sampling | DS | 1 | 75 |
| | 0018,0094 | Percent Phase Field of View | DS | 1 | 71.875 |
| | 0018,0095 | Pixel Bandwidth | DS | 1 | 355 |
| | 0018,1020 | Software Versions | LO | 1 | syngo MR B15 |
| | 0018,1041 | Contrast/Bolus Volume | DS | 1 | 0 |
| | 0018,1044 | Contrast/Bolus Total Dose | DS | 1 | 0 |
| | 0018,1049 | Contrast/Bolus Ingredient Concen | DS | 1 | 0 |
| 413 | 0018,1060 | Trigger Time | DS | 1 | 115 |
| | 0018,1062 | Nominal Interval | IS | 1 | 1011 |
| | 0018,1088 | Heart Rate | IS | 1 | 59 |
| | 0018,1090 | Cardiac Number of Images | IS | 1 | 20 |
| | 0018,1251 | Transmit Coil Name | SH | 1 | Body |
| | 0018,1310 | Acquisition Matrix | US | 4 | 0\256\138\0 |
| | 0018,1312 | In-plane Phase Encoding Directio | CS | 1 | ROW |
| | 0018,1314 | Flip Angle | DS | 1 | 25 |
| | 0018,1315 | Variable Flip Angle Flag | CS | 1 | N |
| | 0018,1316 | SAR | DS | 1 | 0.22843051336938 |
| | 0018,1318 | dB/dt | DS | 1 | 0 |
| | 0018,5100 | Patient Position | CS | 1 | HFS |
| | 0020,000D | Study Instance UID | UI | 1 | 1.3.12.2.1107.5.99.2.1721.30000008041615245393700001113 |
| | 0020,000E | Series Instance UID | UI | 1 | 1.3.12.2.1107.5.99.2.1721.30000008041615245393700001114 |
| | 0020,0011 | Series Number | IS | 1 | 89 |
| | 0020,0012 | Acquisition Number | IS | 1 | 1 |
| | 0020,0013 | Instance Number | IS | 1 | 6 |
| | 0020,1002 | Images in Acquisition | IS | 1 | 41 |
| | 0020,1040 | Position Reference Indicator | LO | 1 | |
| | 0020,1041 | Slice Location | DS | 1 | -23.83494306503 |
| | 0028,0002 | Samples per Pixel | US | 1 | 1 |
| | 0028,0004 | Photometric Interpretation | CS | 1 | MONOCHROME2 |
| | 0028,0006 | Planar Configuration | US | 1 | 0 |
| 415 | 0028,0010 | Rows | US | 1 | 256 |
| 417 | 0028,0011 | Columns | US | 1 | 184 |
| | 0028,0030 | Pixel Spacing | DS | 2 | 0.6861063464837\0.6861063464837 |
| | 0028,0100 | Bits Allocated | US | 1 | 16 |
| | 0028,0101 | Bits Stored | US | 1 | 12 |
| | 0028,0102 | High Bit | US | 1 | 11 |
| | 0028,0103 | Pixel Representation | US | 1 | 0 |
| | 0028,0108 | Smallest Pixel Value in Series | US | 1 | 0 |
| | 0028,0109 | Largest Pixel Value in Series | US | 1 | 4095 |

FIGURE 4C

| Tag | Description | | Content |
|---|---|---|---|
| 0028,1050 | Window Center | DS | 1 -76 |
| 0028,1051 | Window Width | DS | 1 4574 |
| 0028,1052 | Rescale Intercept | DS | 1 -4096 |
| 0028,1053 | Rescale Slope | DS | 1 2 |
| 0028,1054 | Rescale Type | LO | 1 US |
| 0028,1055 | Window Center & Width Explanatio | LO | 1 WINDOW1 |
| 0029,0010 | Private Creator | LO | 1 SIEMENS MEDCOM HEADER |
| 0029,0011 | Private Creator | LO | 1 SIEMENS CSA HEADER |
| 0029,0012 | Private Creator | LO | 1 SIEMENS MEDCOM HEADER2 |
| 0029,0013 | Private Creator | LO | 1 SIEMENS MEDCOM OOG |
| 0029,1031 | PMTF Information 1 | LO | 1 147.0.6061391 |
| 0029,1032 | PMTF Information 2 | UL | 1 94208 |
| 0029,1033 | PMTF Information 3 | UL | 1 0 |
| 0029,1034 | PMTF Information 4 | CS | 1 DBTODICOMNEWBLOB |
| 0029,1108 | Modality Image Header Type | CS | 1 IMAGE NUM 4 |
| 0029,1109 | Modality Image Header Version | LO | 1 20080221 |
| 0029,1118 | Modality Series Header Type | CS | 1 MR |
| 0029,1119 | Modality Series Header Version | LO | 1 20080221 |
| 0029,1260 | Not in Dictionary | LO | 1 com |
| 0029,1308 | Platform OOG Type | CS | 1 MEDCOM OOG 2 |
| 0029,1309 | Platform OOG Version | LO | 1 VX49A |
| 0029,1310 | Platform OOG Info | OB | 1 STEP; |
| 0032,000A | Study Status ID | CS | 1 READ |
| 0032,000C | Study Priority ID | CS | 1 NORMAL |
| 0032,1030 | Reason for Study | LO | 1 ? ? MR - REGURG FRACTION LVEF ; ? SIG INTER ATRIAL SHUNT |
| 0032,1032 | Requesting Physician | PN | 1 NOBODY^^ |
| 0032,1033 | Requesting Service | LO | 1 FMC |
| 0032,1060 | Requested Procedure Description | LO | 1 MR CARDIAC ENHANCED & NONENHAN-CARDIA |
| 0032,4000 | Study Comments | LT | 1 LV FXN I AO FLOW SAT BAND FOR ASD |
| 0040,0244 | Performed Procedure Step Start D | DA | 1 20080221 |
| 0040,0245 | Performed Procedure Step Start T | TM | 1 102921.218000 |
| 0040,0253 | Performed Procedure Step ID | SH | 1 8559750 |
| 0040,0254 | Performed Procedure Step Descrip | LO | 1 MR CARDIAC ENHANCED & NONENHAN-CARDIA |
| 6000,0010 | Overlay Rows | US | 1 256 |
| 6000,0011 | Overlay Columns | US | 1 184 |
| 6000,0015 | Number of Frames in Overlay | IS | 1 1 |
| 6000,0022 | Overlay Description | LO | 1 Siemens MedCom Object Graphics |
| 6000,0040 | Overlay Type | CS | 1 G |
| 6000,0050 | Overlay Origin | SS | 2 1\1 |
| 6000,0051 | Image Frame Origin | US | 1 1 |
| 6000,0100 | Overlay Bits Allocated | US | 1 1 |
| 6000,0102 | Overlay Bit Position | US | 1 0 |

FIGURE 5
536
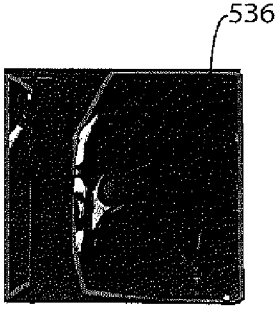
539
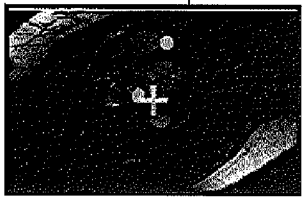
| | Image | Image |
|---|---|---|
| 503 Artifacts | Wrap-Around of surrounding tissue | Distortion Off-Resonance-Effects |
| 506 Reason | Field of View placement in phase encoding wrong | Off-center position of target anatomy |
| 509 Solution | Position FoV correctly | Move table to position anatomy correctly |
516 519

| Image Artifact | Possible Reason | Corrective Action |
|---|---|---|
| Blurry myocardium and chest wall, Ghosting artifacts in phase encoding direction | No or poor breath hold | Repeat scan with breath hold Switch to real-time techniques |
| Cropped heart, aliasing | Field-of-View too small | Increase Field-of-View, change slice position |
| Aliasing of surrounding tissue | Aliasing in phase encoding direction | Swap, rotate phase encoding direction, increase Field-of-View. |
| Low Signal to Noise (SNR) | Not good use of receiver coils | Use appropriate receiver coil elements, replace defective coils |
| Inhomogeneous Blood pool, Banding artifacts, pulsation artifacts | Incorrect carrier frequency, Poor field homogeneity | Shift carrier frequency, perform dedicated shim |
| Myocardium signal not null in delayed enhancement images | Wrong inversion time (TI) | Run TI Scout, Use phase sensitive technique |
| Cardiac images blurry despite breath hold | Poor trigger, arrhythmia | Check ECG signal, swap to a real time imaging strategy |
| Poor dark blood preparation | Data acquisition not in diastole | Modify timing to place data acquisition in diastole, correct echo spacing, readout length |

FIGURE 7B 703 706 709

| Image Artifact | Possible Reason | Corrective Action |
|---|---|---|
| Blurry myocardium and chest wall,<br>Ghosting artifacts in phase encoding direction | No or poor breath hold | Repeat scan with breath hold<br>Switch to real-time techniques |
| Cropped heart, aliasing | Field-of-View too small | Increase Field-of-View, change slice position |
| Aliasing of surrounding tissue | Aliasing in phase encoding direction | Swap, rotate phase encoding direction, increase Field-of-View. |
| Low Signal to Noise (SNR) | Not good use of receiver coils | Use appropriate receiver coil elements, replace defective coils |
| Inhomogeneous Blood pool,<br>Banding artifacts, pulsation artifacts | Incorrect carrier frequency,<br>Poor field homogeneity | Shift carrier frequency, perform dedicated shim |
| Myocardium signal not null in delayed enhancement images | Wrong inversion time (TI) | Run TI Scout,<br>Use phase sensitive technique |
| Cardiac images blurry despite breath hold | Poor trigger, arrhythmia | Check ECG signal, swap to a real time imaging strategy |
| Poor dark blood preparation | Data acquisition not in diastole | Modify timing to place data acquisition in diastole, correct echo spacing, readout length |

SYSTEM FOR DYNAMICALLY IMPROVING MEDICAL IMAGE ACQUISITION QUALITY

This is a non-provisional application of provisional application Ser. No. 61/260,035 filed 11 November, 2009, by S. Zuehlsdorff et al.

FIELD OF THE INVENTION

This invention concerns a system for dynamically improving quality of medical images acquired by a medical imaging device by determining corrected image acquisition parameters for re-acquiring an image

BACKGROUND OF THE INVENTION

The quality of medical images in clinical routine ranges from unacceptable to outstanding and strongly depends on user knowledge, experience and personal engagement. In many cases, images are suboptimal and include artifacts resulting in dissatisfaction on the part of the operator and interpreter of the images and suboptimal reading performance. In a commercial environment the operator of the medical equipment may request advice from the manufacturer of the equipment which results in expensive utilization of experienced personnel. In many cases, the image quality issues are the consequence of user error and inexpert selection of acquisition parameters. Expert advice is expensive and usually not available at the point of need while the subject is being examined. Methods for solving such issues are therefore often only available as a fix for the next time the problem occurs. A system according to invention principles addresses these deficiencies and associated problems.

SUMMARY OF THE INVENTION

A system analyzes medical images and identifies features of compromised image quality and derives and presents to an operator suggested changes in the method of image (e.g., MR, CT scan X-ray) acquisition of the images in order to optimize the quality of the generated images. A system dynamically improves quality of medical images acquired by a medical imaging device using at least one processing device. The at least one processing device includes an image analyzer, a correction processor and a message generator. The image analyzer automatically parses and analyzes data representing an image of a particular anatomical feature of a patient acquired by a medical image acquisition device to identify defects in the image by examining the data representing the image for predetermined patterns associated with image defects. The correction processor uses a predetermined information map associating image defects with corresponding corrective image acquisition parameters to determine corrected image acquisition parameters for use in re-acquiring an image using the image acquisition device in response to an identified defect. The message generator generates a message for presentation to a user indicating an identified defect and suggesting use of the corrected image acquisition parameters for re-acquiring an image.

BRIEF DESCRIPTION OF THE DRAWING

FIGS. 2 and 3 illustrate reference defect free images and exemplary defective images exhibiting typical image artifacts together with associated tabular information identifying artifacts, reasons for defective image acquisition and corrective action for use in re-acquiring images, according to invention principles.

FIGS. 4A, 4B, 4C show a DICOM header indicating image acquisition settings used for comparison with comparable settings of acquired sub-optimal and defective images, according to invention principles.

FIG. 5 illustrates detection of anatomical landmarks for assessing correct placement of an anatomical target structure in an image scanner, according to invention principles.

FIGS. 7A and 7B shows a map associating image defects, error reasons and corrective actions, according to invention principles.

DETAILED DESCRIPTION OF THE INVENTION

A system dynamically improves medical image acquisition quality by monitoring and automatically identifying and correcting imaging defects by altering image acquisition device settings. The system automatically analyzes an image exhibiting suboptimal quality and compares parameters and image acquisition settings of the image with corresponding parameters and settings of a known defect free reference image. The system indicates (and in one embodiment automatically implements) changes in image acquisition device settings or the way an imaging application (e.g., for post-processing of an acquired image) is being used to improve image acquisition. Inexperienced users have limitations in identifying different classes of imaging artifacts and in deriving steps to eliminate the artifacts that may be determinable by an experienced user. The system identifies and corrects image acquisition error and user error and supports image device operation by an inexperienced user. The system enables an inexperienced user to improve image quality by prompting a user with substantially immediate suggestions of imaging protocol parameters and setting changes without the delay of involvement of a remote expert support team.

The system automatically identifies image defects (or artifacts) using an Image analyzer in a stand-alone environment (e.g. on a PC, notebook, PDA or other processing device) or fully integrated into an image acquisition device image reconstruction system. This Image analyzer employs image post processing methods to identify artifacts such as outer body detection. The system translates an identified defect (artifact) into an error reason using an error log in one embodiment. An identified defect is reported in an error log, such as a simple file recording reported error messages and including specific information about a detected defect. This may include (but is not limited to) number of detected defects, nature of the defect and severity. This classification can be used as parameters to query a data base to identify appropriate corrective action. Although the invention is described herein in the context of an MR imaging system, this is exemplary only and the invention principles are also applicable to other types of imaging system including, X-ray, CT scan and Ultrasound, for example.

Figure 1:
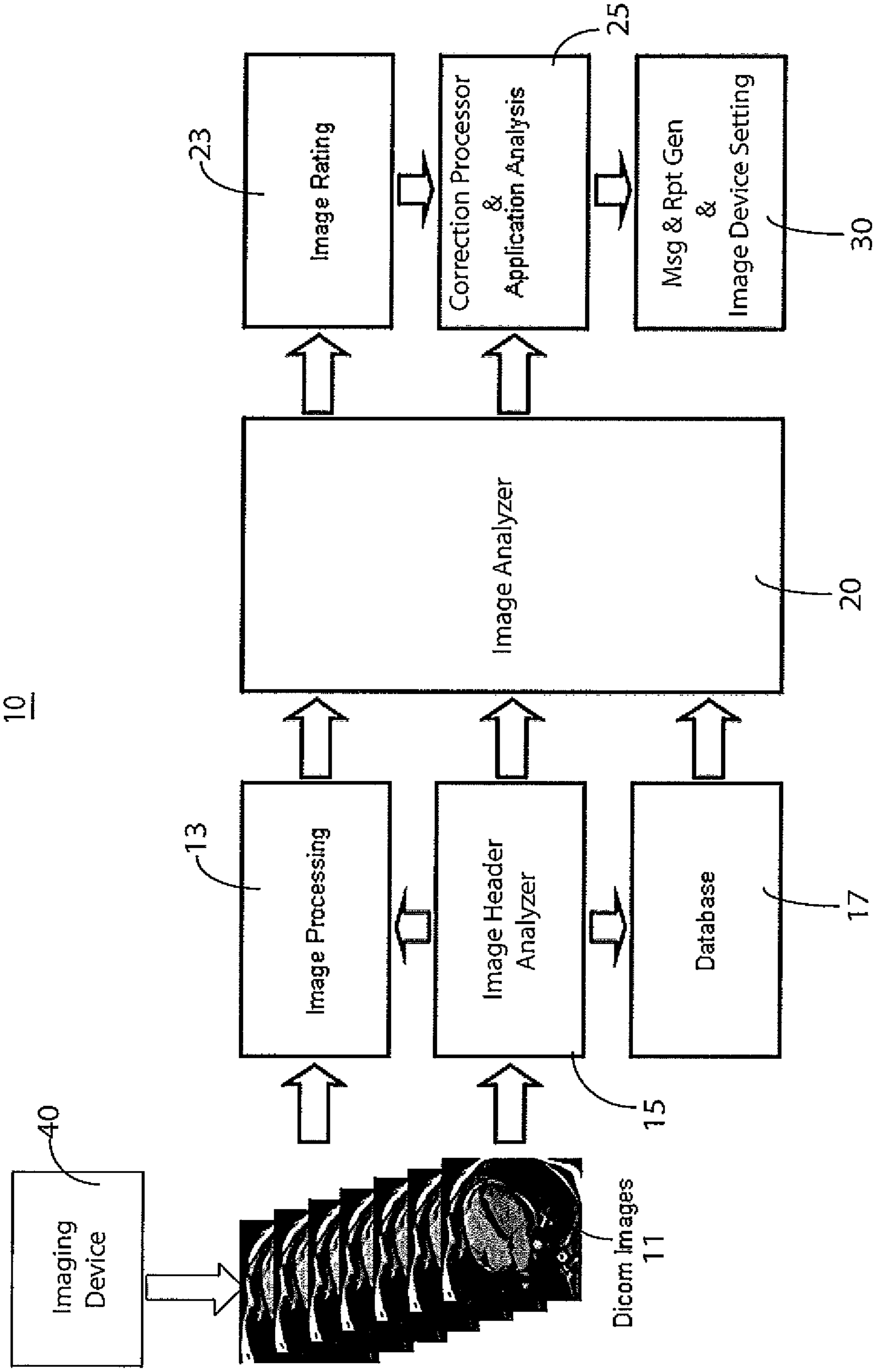
FIG. 1 shows a system for dynamically improving quality of medical images acquired by a medical imaging device, according to invention principles.

FIG. 1 shows system 10 for dynamically improving quality of medical images acquired by medical imaging device 40. DICOM and other images 11 containing undesired image artifacts or exhibiting compromised image quality acquired by imaging device 40 are processed by an image processing unit 13. Image header analyzer and DICOM header reader 15 retrieves image related information such as imaging modality type of device 40 (e.g. Magnetic Resonance, Computed Tomography), body region (e.g. abdomen, head), imaging protocol (e.g. dark blood prepared turbo spin echo for MR imaging) and related imaging parameters (e.g., echo time TE, repetition time TR, inversion time TI) as well as physiological parameters (e.g., heart rate, respiratory rate). Database 17 contains a library of medical images for different types of modalities (e.g., MR, CT scan, X-ray, Ultrasound) and clinical applications that serve as a gold standard for image quality and artifacts.

FIGS. 4A, 4B, 4C show a DICOM header indicating image acquisition settings used for comparison with comparable settings of acquired sub-optimal and defective images. DICOM image data represents a clinical standard that consists of pixel data comprising an image) and a data header that contains information about the image. FIGS. 4A, 4B, 4C show typical DICOM header information elements including highlighted items used by system 10 for comparison with image acquisition settings. DICOM header reader 15 retrieves image related information items 403, 406, 409, 410, 413, 415 and 417, for example. Information items 403, 406, 409, 410, 413, 415 and 417 comprise, Modality, manufacturer and model, Contrast/Bolus Agent, Scanning Sequence, Sequence Variant, Scan Options, MR Acquisition Type, Name, Flag, Slice Thickness, Repetition Time, Echo Time, Number of Averages, Imaging Frequency, Imaged Nucleus, Echo Numbers, Magnetic Field Strength, Number of Phase Encoding Steps, Echo Train Length, Percent Sampling, Percent Phase Field of View, Pixel Bandwidth, Software Versions, Contrast/Bolus Volume, Contrast/Bolus Total Dose, Bolus Ingredient Concentration, Trigger Time, Nominal Interval, Heart Rate, Cardiac Number of Images, Transmit Coil Name, Acquisition Matrix, In-plane Phase Encoding Direction, Flip Angle, Variable Flip Angle Flag, SAR, dB/dt and number of rows and columns of an Image. The DICOM information extracted by image header analyzer 15 is stored in database 17 and used by image analyzer 20 to identify suitable template reference images for use in comparison with acquired images and imaging acquisition parameters and settings for improved acquisition of images.

Image analyzer 20 automatically parses and analyzes data representing an image of a particular anatomical feature of a patient acquired by medical image acquisition device 40 to identify defects in the image by examining the data representing the image for predetermined patterns associated with image defects. Image analyzer 20 processes data retrieved from database 17 representing acquired images 11 using the predetermined stored knowledge of an image acquisition clinical application extracted from the DICOM header. Depending on the application, the images are analyzed in order to identify specific classes of potential artifacts or image quality problems that may occur for a particular clinical application. For MR images analyzer 20 analyzes image data retrieved from database 17 to determine image characteristics by, for example, determining noise in an image, image contrast, aliasing, off-resonance effects, imaging slice orientation/ and position, e.g., determining whether a relevant organ is correctly positioned in the iso-center of a sufficiently large field of view and consistency of settings and parameters over multiple slices (e.g. for a stack of parallel images).

Analyzer 20 further analyzes image data retrieved from database 17 to determine image characteristics by, identifying artifacts including ghosting and blurring and determines image homogeneity, imaging parameters (e.g., RF coil selection, timings, bandwidth) and hardware problems (e.g. spikes). Image analyzer 20 compares the determined characteristics with corresponding characteristics of gold standard images and image acquisition parameters of the reference images and generates a list identifying items that are outside of a predetermined acceptable range (e.g. a specific type of artifact may be inevitable but becomes intrusive at a certain level determined by a threshold).

An image rating processor 23 ranks individual items of the image evaluation list as mild, severe or clinically unacceptable, for example, using a metric of reference data. FIG. 5 illustrates detection of anatomical landmarks for assessing correct placement of an anatomical target structure in an image scanner. Some artifacts can be detected by analyzing imaging parameters alone, many artifacts however require analysis of contents of an image to detect the artifacts. The analysis may involve applying predetermined knowledge indicating an understanding of an imaged portion of anatomy. Analyzer 20 reliably provides automatic detection of outer body elements and relevant field of view and also detects wrap-around artifacts as indicated by image 536, using known methods. Analyzer 20 separates an image into a foreground and background region, enabling global analysis of the image for defects and quality indicators e.g. SNR (signal to noise ratio) using known methods. Analyzer 20 also detects anatomical landmarks for assessing correct placement of an anatomical target structure in an image as illustrated in image 539. In response to detection of relevant target, this information is used to locally analyze the image content to assess contrast to noise ratio, edge strength, SNR, and other measures indicating image quality. Other known image processing means are employed to assess presence of artifacts in MR images, including region-based analysis, learning based solutions to detect image-based, wavelet-based, or spectral signatures of certain artifact patterns and including analysis of deformation fields to characterize motion in time-resolved datasets.

In FIG. 5, the tabular information identifies an artifact in row 503, a candidate reason for the artifact in row 506 and corrective action to re-acquire a defect free image in row 509. Column 516 indicates image 536 shows an artifact comprising wrap around of surrounding tissue due to an incorrect placement of a Field of View (FOV) in phase encoding that may be corrected by correctly positioning the FOV. Column 519 indicates image 539 shows distortion resulting from off-resonance effects due to an off-center position of target anatomy that may be corrected by moving a patient support table to correctly position the anatomy.

Correction processor 25 uses predetermined stored knowledge of an image acquisition clinical application extracted from a DICOM header as well as image rating data to derive candidate suggestions for corrective image acquisition parameters. Specifically, correction processor 25 uses a predetermined information map associating image defects with corresponding corrective image acquisition parameters to determine corrected image acquisition parameters for use in re-acquiring an image using image acquisition device 40 in response to an identified defect.

The determined corrected image acquisition parameters improve image quality for a repeated scan or for a next image study performed automatically or in response to user interaction. In one embodiment, a user may visually determine an image artifact and suboptimal quality and support image analysis by selecting a best match artifact example from a selection of candidate manifestations of an artifact pattern. In another embodiment, a user may select optimized image acquisition parameters used in acquisition of a set of sample images and system 10 indicates expected image changes by a text message in response to modification of a particular parameter. Correction processor 25 prompts a user with corrected MR image acquisition parameters for use in re-acquiring an image including, for example to, use breath hold and monitor breathing of a patient, check for arrhythmia, re-calibrate a center frequency, use a larger field-of-view (FOV) and use changed imaging parameters values for TE, TR and TI, inject contrast agent and to use different RF receiver coils, for example. Suggested candidate image acquisition parameters are presented to a user in an explicit way (e.g., via a dialog box). Correction processor 25 also provides subtle hints to a user that do not interfere with user operation in response to analysis by unit 20 identifying an image acquisition parameter setting as being suboptimal. A hint may be presented by visual markup similar to an underline of the 'check as you type' feature of Microsoft Word™ or by using another different type of visual attribute, such as color, highlighting, shading, symbols or text, for example. Correction processor 25 also analyzes determined imaging characteristics to identify application dependent conflicting parameters. Known systems determine parameter settings based on the ability of scanner hardware, for example, to realize such settings. In contrast, in response to image acquisition characteristic analysis, correction processor 25 selects parameters based on suitability for a designated clinical imaging application.

Message and report generator 30 generates a message for presentation to a user indicating an identified defect and suggesting use of corrected image acquisition parameters for re-acquiring an image. Unit 30 also provides a report that summarizes detected issues concerning image quality and corresponding suggestions for changed image acquisition parameters. A report in one embodiment is a simple text output or becomes visible as a warning to the operator as a "pop-up" if an image quality score exceeds a certain threshold, for example. In another embodiment, changes in image acquisition parameters are automatically made to a stored protocol in image seamier database 17. In a further embodiment a report is sent to a service center for remote diagnosis and optimization of acquisition settings (by user or automatically) and to extend a database of template images.

FIGS. 2 and 3 illustrate reference defect free functional cardiac images and exemplary defective images exhibiting typical MR image artifacts together with associated tabular information identifying artifacts, reasons for defective image acquisition and corrective action for use in re-acquiring images. Artifacts often manifest in a specific appearance of images that are identified by system 10 by comparison with template image artifacts for a comparable clinical application such as by identifying banding artifacts based on repetitive band-like changes in luminance using known luminance edge and transition detection methods. The system further determines from predetermined information in a map associating artifacts with reasons for a problem and with corrective action, the reason for compromised image quality and settings and other changes to improve image quality.

In FIG. 2, image 233 is a defect free reference image and images 236, 239 and 242 show typical artifacts. The tabular information identifies an artifact in row 203, a candidate reason for the artifact in row 206 and corrective action to re-acquire a defect free image in row 209. Column 216 indicates image 236 shows a blurry myocardium and chest wall due to poor breath hold that may be corrected by re-acquiring the image during patient breath hold. Column 219 indicates image 239 shows a cropped heart and aliasing due to a Field of View (FOV) being too small that may be corrected by re-acquiring the image with an enlarged FOV and a corrected imaging slice position. Column 221 indicates image 242 shows aliasing of heart surrounding tissue due to an incorrect phase encoding direction that may be corrected by re-acquiring the image with a correct phase encoding direction (e.g., Anterior-posterior).

In FIG. 3, image 333 is a defect free reference image and images 336, 339 and 342 show typical artifacts. The tabular information identifies an artifact in row 303, a candidate reason for the artifact in row 306 and corrective action to re-acquire a defect free image in row 309. Specifically, column 316 indicates image 336 shows aliasing of cardiac surrounding tissue due to a FOV in a phase encoding (PE) direction being too small that may be corrected by re-acquiring the image with an increased FOV in the PE direction. Column 319 indicates image 339 shows a low signal to noise ratio due to use of inappropriate RF coils in MR imaging that may be corrected by re-acquiring the image using appropriate RF receiver coils having correct coil location. Column 321 indicates image 342 shows an inhomogeneous blood pool as well as pulsation artifacts and banding artifacts due to an incorrect RF earner frequency that may be corrected by use of a correct RF carrier frequency and use of a frequency scout to identify a correct carrier frequency.

Figure 6:
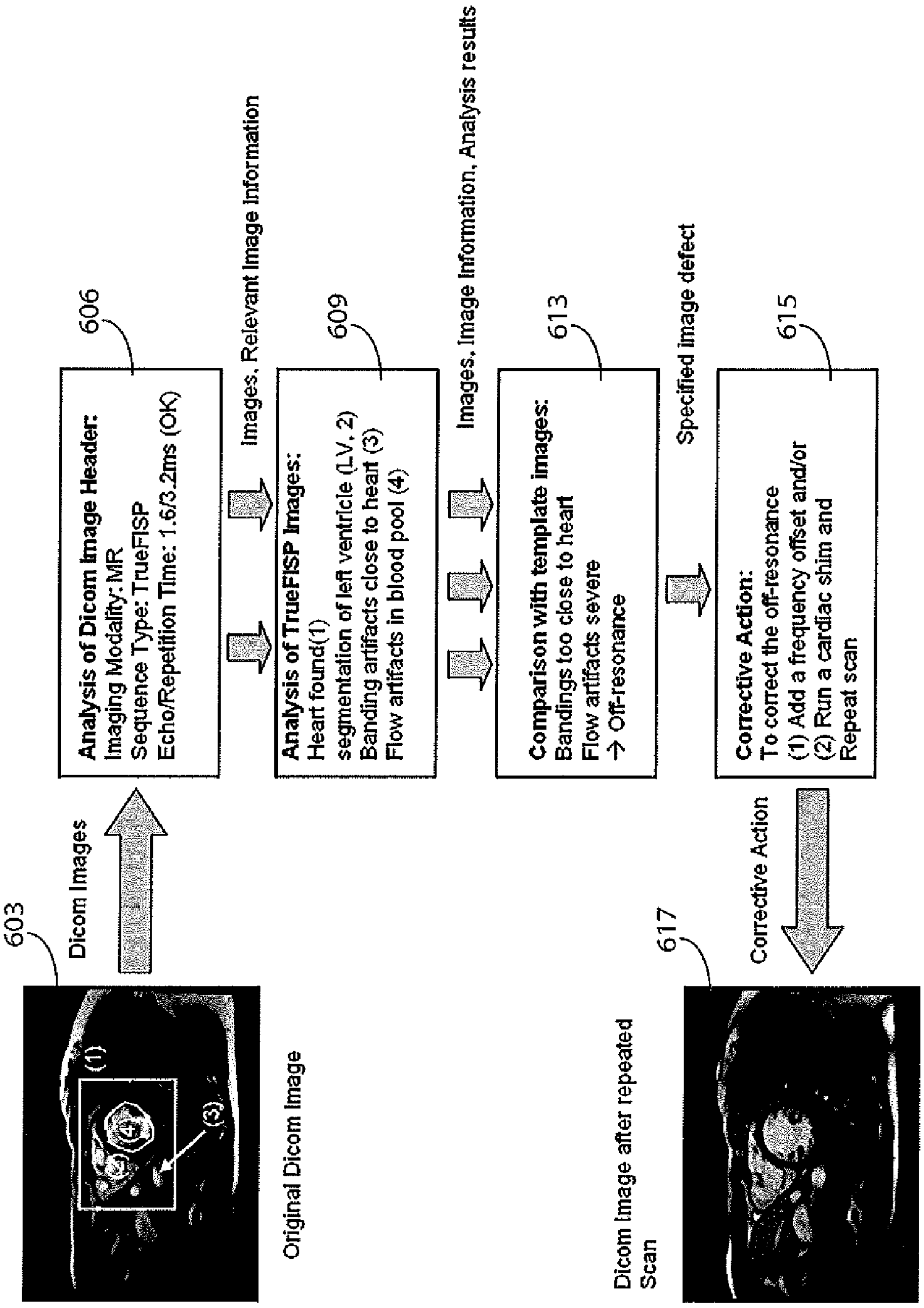
FIG. 6 shows a flowchart of a process performed by a system for dynamically improving quality of medical images by identifying image defects, corresponding reasons for error and by translating identified error reasons into corrective action, according to invention principles.

FIG. 6 shows a flowchart of a process performed by a system for dynamically improving quality of medical images by identifying image defects, corresponding reasons for error and by translating identified error reasons into corrective action. Image header analyzer and DICOM header reader 15 (FIG. 1) in step 606 analyzes a DICOM header of image 603 and retrieves image acquisition parameters indicating an MR imaging modality type, a TrueFISP (True fast imaging with steady state precession) pulse sequence and an Echo/Repetition time of 1.6/3.2 ins. In step 609, analyzer 20 analyzes the content of TrueFISP image 603 and detects segmentation of a heart left ventricle, banding artifacts close to the heart and flow artifacts in a blood pool. Image analyzer 20 automatically identifies image artifacts using known image processing methods and predetermined information associating particular image characteristics with known defects types. For example, analyzer 20 in step 613 in one embodiment, identifies banding artifacts by image analysis looking for bands of relatively constant luminance separated by relatively constant distance in image data by comparing image features with a template known banding pattern using scaling, translation and rotation functions to iteratively match a template with an image feature. Analyzer 20 also compares image acquisition parameters with DICOM header parameter information and with a reference defect free image and with an image showing a matched template artifact characteristic such as a template known banding pattern for a TrueFISP image having comparable acquisition characteristics for a comparable clinical application and anatomical region. The DICOM header parameter information is also retrieved from database 17 and analyzer 20 automatically determines image 603 shows banding too close to a heart and blood flow artifacts.

Analyzer 20 matches artifacts with a reason for the artifacts using predetermined information shown in FIGS. 7A and 7B in a map associating artifacts in column 703 with reasons for a problem in column 706 and with corrective action in column 709. System 10 translates an identified defect into an error reason based on predetermined information comprising a map associating one or more combinations of defect with error reasons. The map may be in the form of tabular association or another format. The system further translates an error reason into corrective action involving providing improved image acquisition parameters for image acquisition by an imaging device. In step 615, correction processor 25 uses the map of FIG. 7 as well as image acquisition parameters (indicating MR imaging modality type, a TrueFISP pulse sequence and Echo/Repetition time of 1.6/3.2 ms) derived by image header data analyzer 15 as well as image rating data determined by image rating processor 23 to determine corrective action. The rating data ranks artifacts including ghosting and blurring and imaging parameters as mild, severe or clinically unacceptable. Analyzer 20 and correction processor 25 uses the data of row 712, for example, of FIG. 7A in associating the artifact with a reason for the artifact (incorrect carrier frequency and poor field homogeneity) and corrective action (shift the carrier frequency and perform a field shim). System 10 re-acquires the image using imaging device 40 using the corrective action to provide corrected image 617.

In one embodiment, system 10 presents an error message to a user using a computer operating system e.g. in a pop-up window. An error message indicates nature of image artifact and severity. The system determines if a corrective action is known, and if it is, suggests corrective action for a repeated scan, using changed specific imaging parameters. In one embodiment an imaging device framework using the system examines an error message, to determine it is recommended to repeat an imaging scan and automatically changes appropriate imaging parameters based on determined corrective action.

Figure 8:
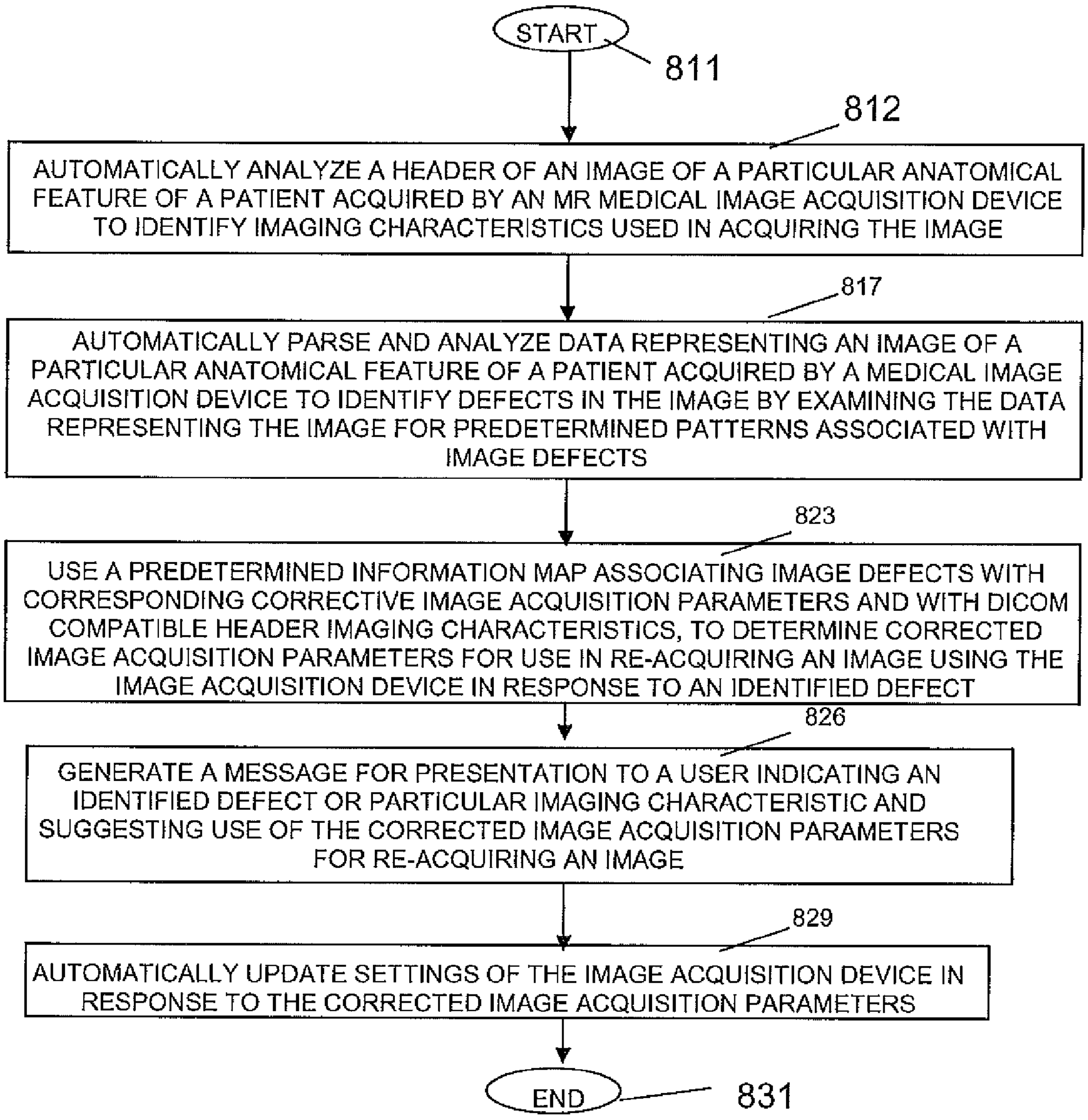
FIG. 8 shows a flowchart of a process performed by the system for dynamically improving quality of medical images acquired by a medical imaging device, according to invention principles.

FIG. 8 shows a flowchart of a process performed by system 10 for dynamically improving quality of medical images acquired by a medical imaging device. In step 812 following the start at step 811, image metadata (e.g., header) data analyzer 15 automatically analyzes a header of an image (e.g., DICOM compatible image header data) of a particular anatomical feature of a patient acquired by an MR medical image acquisition device to identify imaging characteristics used in acquiring the image. Metadata comprises data concerning an image and includes header data, for example. Header analyzer 15 compares the identified imaging characteristics with corresponding imaging characteristics in a template header of a defect free image of the particular anatomical feature and acquired using an imaging modality device of the same type, to identify differences.

In step 817 image analyzer 20 automatically parses and analyzes data representing an image of a particular anatomical feature of a patient acquired by medical image acquisition device 40 to identify defects in the image by examining the data representing the image for predetermined patterns associated with image defects. Image analyzer 20 automatically selects the predetermined patterns from multiple predetermined patterns associated with multiple known defect types in response to a type of imaging modality device, the identified imaging characteristics and data identifying the particular anatomical feature. Image analyzer 20 automatically parses and analyzes data representing the image to identify patterns associated with at least one of, (i) banding, (ii) aliasing and (iii) off-resonance effects. Image analyzer 20 automatically parses and analyzes data representing the image to identify defects associated with at least one of, (a) noise, (b) image contrast, (c) slice position, (d) slice orientation, (e) blurring, (0 ghosting, (g) image homogeneity and (h) field of view. Image analyzer 20 further automatically parses and analyzes data representing the image to identify defects associated with, positioning of the anatomical feature in the image, MR device coil selection, pulse sequence timing and image consistency over multiple stacked slices.

Correction processor 25 in step 823, uses a predetermined information map associating image defects with corresponding corrective image acquisition parameters, corresponding defect messages describing defects, differences in DICOM compatible header imaging characteristic between a defective image and a defect free image and with DICOM compatible header imaging characteristics, to determine corrected image acquisition parameters for use in re-acquiring an image using image acquisition device 40 in response to an identified defect. A message generator in step 826, generates a message for presentation to a user including a defect message associated with an identified defect derived using the predetermined information map and indicating an identified defect, particular imaging characteristic and an identified difference between header data of acquired and defect free images and suggesting use of the corrected image acquisition parameters for re-acquiring an image, in response to an identified difference exceeding a predetermined threshold. In one embodiment, a message indicates a reason for occurrence of a corresponding defect. In step 829 an image device setting unit in correction processor 30 automatically updates settings of the image acquisition device in response to the corrected image acquisition parameters. Image metadata data analyzer 15 analyzes metadata of an image by comparing individual metadata items with corresponding predetermined ranges to identify metadata items exceeding the ranges. A user interface generator in unit 30 automatically generates data representing a display image visually identifying at least one cause of a defect in the image and prompts a user with a resolution action or acquisition parameters to reduce the defect in the image The process of FIG. 8 terminates at step 831.

A processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a computer, controller or microprocessor, for example, and is conditioned using executable instructions to perform special purpose functions not performed by a general purpose computer. A processor may be coupled (electrically and/or as comprising executable components) with any other processor enabling interaction and/or communication therebetween. A user interface processor or generator (in unit 30 FIG. 1) is a known element comprising electronic circuitry or software or a combination of both for generating display images or portions thereof. A user interface comprises one or more display images enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A user interface (UI), as used herein, comprises one or more display images, generated by a user interface processor and enabling user interaction with a processor or other device and associated data acquisition and processing functions.

The UI also includes an executable procedure or executable application. The executable procedure or executable application conditions the user interface processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

The system and processes of FIGS. 1-8 are not exclusive. Other systems and processes may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. The system automatically identifies image artifacts and uses predetermined information in a map in translating an identified artifact into an error reason and corrective action for use in re-acquiring an image. Further, the processes and applications may, in alternative embodiments, be located on one or more (e.g., distributed) processing devices on a network linking the units of FIG. 1. Any of the functions, image controls and steps provided in FIGS. 1-8 may be implemented in whole or in part in hardware, software or a combination of both.

What is claimed is:

1. A system for dynamically improving quality of medical images acquired by a medical imaging device, comprising:
at least one processing device including:
an image analyzer for automatically parsing and analyzing data representing an image of a particular anatomical feature of a patient acquired by a medical image acquisition device to identify defects in said image due to image acquisition settings by examining said data representing said image for predetermined patterns associated with image defects;
a correction processor for using a predetermined information map associating image defects with corresponding corrective image acquisition parameters to determine corrected image acquisition parameters for use in re-acquiring an image using said medical image acquisition device in response to an identified defect; and
a message generator for generating a message for presentation to a user indicating an identified defect and suggesting use of said corrected image acquisition parameters for re-acquiring an image using said medical image acquisition device.

2. A system according to claim 1, wherein
said correction processor uses a predetermined information map associating image defects with corresponding corrective image acquisition parameters and with corresponding defect messages describing defects and
said message generator generates a message for presentation to a user including a defect message associated with an identified defect derived using said predetermined information map.

3. A system according to claim 2, wherein
said defect messages indicate a reason for occurrence of a corresponding defect.

4. A system according to claim 2, wherein
said image header data is DICOM (Digital Imaging and Communications in Medicine) compatible image header data.

5. A system according to claim 1, including
an image header data analyzer for analyzing a header of said image to identify imaging characteristics used in acquiring said image and
said image analyzer automatically selects said predetermined patterns from a plurality of predetermined patterns in response to the identified imaging characteristics.

6. A system according to claim 1, wherein
said image analyzer automatically selects said predetermined patterns from a plurality of predetermined patterns associated with a plurality of known defect types in response to a type of imaging modality device.

7. A system according to claim 1, wherein
said image analyzer automatically selects said predetermined patterns from a plurality of predetermined patterns in response to data identifying said particular anatomical feature.

8. A system according to claim 1, including
an image metadata data analyzer for analyzing metadata of said image by comparing individual metadata items with corresponding predetermined ranges to identify metadata items exceeding said ranges.

9. A system according to claim 1, including
a user interface generator for automatically generating data representing a display image visually identifying at least one cause of a defect in said image.

10. A system according to claim 9, wherein
said display image prompts a user with a resolution action or acquisition parameters to reduce said defect in said image.

11. A system for dynamically improving quality of medical images acquired by a medical imaging device, comprising:
at least one processing device including:
an image analyzer for automatically parsing and analyzing data representing an image of a particular anatomical feature of a patient acquired by a medical image acquisition device to identify defects in said image by examining said data representing said image for predetermined patterns associated with image defects;
a correction processor for using a predetermined information map associating image defects with corresponding corrective image acquisition parameters to determine corrected image acquisition parameters for use in re-acquiring an image using said image acquisition device in response to an identified defect;
a message generator for generating a message for presentation to a user indicating an identified defect and suggesting use of said corrected image acquisition parameters for re-acquiring an image; and an image header data analyzer for analyzing a header of said image to identify imaging characteristics used in acquiring said image and comparing the identified imaging characteristics with corresponding imaging characteristics in a template header of an image of said particular anatomical feature and acquired using an imaging modality device of the same type, to identify differences and said message generator generates a message indicating an identified difference for presentation to a user.

12. A system according to claim 2, wherein said image header data analyzer generates a message indicating an identified difference for presentation to a user in response to an identified difference exceeding a predetermined threshold.

13. A system according to claim 1, including an image device setting unit for automatically updating settings of said image acquisition device in response to said corrected image acquisition parameters.

14. A system for dynamically improving quality of medical images acquired by an MR (Magnetic Resonance) medical imaging device, comprising:

at least one processing device including:

an image data analyzer for automatically analyzing metadata of an image of a particular anatomical feature of a patient acquired by an MR medical image acquisition device to identify imaging acquisition related characteristics used in acquiring said image;

an image analyzer for automatically parsing and analyzing data representing an image of a particular anatomical feature of a patient acquired by a medical image acquisition device to identify defects in said image by examining said data representing said image for predetermined patterns associated with image defects;

a correction processor for using a predetermined information map associating image defects with corresponding corrective image acquisition parameters and with DICOM (Digital Imaging and Communications in Medicine) compatible header imaging characteristics, to determine corrected image acquisition parameters for use in re-acquiring an image using said image acquisition device in response to an identified defect; and an image device setting unit for automatically updating settings of said image acquisition device in response to said corrected image acquisition parameters;

a message generator for generating a message for presentation to a user indicating an identified defect or particular imaging characteristic and suggesting use of said corrected image acquisition parameters for re-acquiring an image.

15. A system according to claim 14, wherein said image data analyzer compares the identified imaging characteristics with corresponding imaging characteristics in a template header of an image of said particular anatomical feature and acquired using an imaging modality device of the same type, to identify differences and said correction processor uses a predetermined information map associating differences in DICOM compatible header imaging characteristic between a defective image and a defect free image, with corresponding corrective image acquisition parameters to determine corrected image acquisition parameters for use in re-acquiring an image using said image acquisition device in response to an identified difference.

16. A system according to claim 14, wherein said image analyzer automatically parses and analyzes data representing said image to identify patterns associated with at least one of, (a) banding, (b) aliasing and (c) off-resonance effects.

17. A system according to claim 14, wherein said image analyzer automatically parses and analyzes data representing said image to identify defects associated with at least one of, (a) noise, (b) image contrast, (c) slice position and (d) slice orientation.

18. A system according to claim 14, wherein said image analyzer automatically parses and analyzes data representing said image to identify defects associated with at least one of, (a) blurring, (b) ghosting, (c) image homogeneity and (d) field of view.

19. A system according to claim 14, wherein said image analyzer automatically parses and analyzes data representing said image to identify defects associated with at least one of, (a) positioning of said anatomical feature in said image, (b) MR device coil selection, (c) pulse sequence timing and (d) image consistency over a plurality of stacked slices.

20. A system according to claim 14, including an error message generator for generating error messages identifying a number of detected defects and nature of an individual defect.

21. A system for dynamically improving quality of medical images acquired by a medical imaging device, comprising:

at least one processing device including:

an image header data analyzer for automatically analyzing a DICOM (Digital Imaging and Communications in Medicine) compatible header of an image of a particular anatomical feature of a patient acquired by a medical image acquisition device to identify imaging acquisition related characteristics used in acquiring said image and comparing the identified imaging characteristics with corresponding imaging characteristics in a template header of an image of said particular anatomical feature and acquired using an imaging modality device of the same type, to identify differences;

a correction processor for using a predetermined information map associating DICOM compatible header imaging characteristics with corresponding corrective image acquisition parameters to determine corrected image acquisition parameters for use in re-acquiring an image using said image acquisition device in response to an identified difference; and a message generator for generating a message for presentation to a user indicating an identified difference and suggesting use of said corrected image acquisition parameters for re-acquiring an image.

22. A system according to claim 21, including an image analyzer for automatically parsing and analyzing data representing an image of a particular anatomical feature of a patient acquired by a medical image acquisition device to identify defects in said image by examining said data representing said image for predetermined patterns associated with image defects, said correction processor uses a predetermined information map associating image defects with corresponding corrective image acquisition parameters to determine corrected image acquisition parameters for use in re-acquiring an image using said image acquisition device in response to an identified defect; and said message generator generates a message for presentation to a user indicating an identified defect and suggesting use of said corrected image acquisition parameters for re-acquiring an image.

* * * * *